(12) United States Patent
Huntington et al.

(10) Patent No.: US 8,672,172 B2
(45) Date of Patent: Mar. 18, 2014

(54) ORGANIZER SYSTEM

(75) Inventors: Elysha Huntington, New York, NY (US); Anthony B. Gallo, Warren, NJ (US); David Lutness, Belle Mead, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 639 days.

(21) Appl. No.: 11/881,675

(22) Filed: Jul. 27, 2007

(65) Prior Publication Data
US 2009/0026209 A1    Jan. 29, 2009

(51) Int. Cl.
*B65D 1/24* (2006.01)
(52) U.S. Cl.
CPC .................................. *B65D 1/24* (2013.01)
USPC ......... 220/523; 220/505; 220/553; 206/459.5
(58) Field of Classification Search
USPC .............. 220/500, 503, 505, 507, 523, 521; 206/459.5, 440, 438, 494, 812, 823, 206/232
See application file for complete search history.

(56) References Cited

U.S. PATENT DOCUMENTS

| | | | | |
|---|---|---|---|---|
| 1,648,648 | A * | 11/1927 | Lilleston | |
| 3,743,088 | A * | 7/1973 | Henkin | 206/569 |
| 5,082,113 | A * | 1/1992 | Romick | 206/459.1 |
| 5,323,926 | A * | 6/1994 | Pomroy et al. | 220/526 |
| 5,738,241 | A * | 4/1998 | McEntee | 220/532 |
| 5,788,072 | A * | 8/1998 | Chen | 206/372 |
| 5,848,700 | A * | 12/1998 | Horn | 206/570 |
| 5,857,583 | A * | 1/1999 | Chantaca et al. | 220/523 |
| 5,950,834 | A * | 9/1999 | Woodnorth et al. | 206/541 |
| 6,415,924 | B1 * | 7/2002 | Lee | 206/459.5 |
| 6,622,856 | B2 * | 9/2003 | Gallo et al. | 206/232 |
| 6,640,976 | B1 * | 11/2003 | Franks-Farah et al. | 206/571 |
| 6,740,068 | B1 * | 5/2004 | Aruffo et al. | 604/355 |
| 8,387,794 | B2 * | 3/2013 | Stitzlein | 206/427 |
| 2002/0079240 | A1 * | 6/2002 | Beard Kelley et al. | 206/232 |
| 2003/0042170 | A1 * | 3/2003 | Bolanos | 206/570 |
| 2003/0136704 | A1 * | 7/2003 | Burgess | 206/581 |
| 2004/0031799 | A1 * | 2/2004 | Dege et al. | 220/523 |
| 2005/0092647 | A1 * | 5/2005 | McBain | 206/570 |
| 2005/0150809 | A1 * | 7/2005 | Pile | 206/570 |
| 2006/0124648 | A1 * | 6/2006 | Croft et al. | 220/521 |
| 2007/0007164 | A1 * | 1/2007 | Lord | 206/570 |
| 2008/0099485 | A1 * | 5/2008 | Holbrook et al. | 220/507 |
| 2013/0126387 | A1 * | 5/2013 | Rowe | 206/553 |

OTHER PUBLICATIONS

"Small plastic compartment boxes, and large metal trays shown" in http://www.boltdepot.com/us-assortments.aspx, date unknown.
"Air Conditioning Nitrile O-Rings—196 Pieces" and other related articles shown in http://www.nutsandbolts.com/assortments-c-29.html?gclid=CPP-efMzaECFYNd5QodOkoZIg, date unknown.

* cited by examiner

*Primary Examiner* — Robert J Hicks
*Assistant Examiner* — Kareen Rush

(57) ABSTRACT

A system for organizing very similar articles in a container so that the user can readily identify the desired article. A "menu" may be used to readily identify the articles, which preferably are non-food, consumer items, such as bandages or first-aid supplies. The "menu" may be provided in the lid of the container. If desired, the "menu" may be fixedly provided in the lid of the container, such as on the interior-facing surface of a flip-top or hinged-lid of the container. The articles may be organized in an insert or tray that is removable from a shell portion of the container so the shell can be used for other purposes.

14 Claims, 5 Drawing Sheets

ORGANIZER SYSTEM

FIELD OF THE INVENTION

The present invention relates to an organizer system designed to organize a plurality of different items that are very similar in appearance and to provide a user with guidance in identifying a desired one of the plurality of different items. The present invention further relates to a manner of facilitating identification of a desired one of a plurality of different items.

BACKGROUND OF THE INVENTION

Various organizer systems are known in the art for organizing different types of articles in an organizer or other type of holder or container or case. Such organizer systems generally organize the articles according to type, separating one from the other such as within different compartments. For instance, a plurality of similar articles may be placed in each compartment, the articles in one compartment differing from the articles in the other compartment so that the compartments serve to organize the articles by type.

Difficulties arise with organizer systems for articles that are different from each other but which are not readily distinguishable from one another, either because of their appearance or because of their arrangement within the compartments. For instance, existing organizers that separate a plurality of different types of similar-looking articles (different articles that nonetheless are not readily distinguishable from one another) by grouping articles of the same type separately from articles of a different type have not been known to provide a ready means of readily distinguishing the different articles from one another. Thus, even though the user may feel assured that all articles in a given compartment are of a same type, the user may not know what that type of article actually is because such article is not readily distinguishable from an article or articles in other compartments in the organizer system.

Moreover, various packagings are known for containing a plurality of different types of articles that are not readily distinguishable from one another in a manner that does not expose the articles for ready identification. For instance, articles that are not marked along a given side may be arranged with only such unmarked side readily visible. The articles must be individually removed from the packaging and examined to determine the identity of the article. Such packagings have not been known to provide a ready means of distinguishing the different articles from one another without removing the articles and examining the articles. Such problem is exacerbated when the articles are tightly packed in the packaging and need to be pulled out and examined to differentiate one article from the other, possibly disturbing the other articles in the packaging. Even more challenging are packages of different types of articles that do not bear any identifying indicia for differentiating among the different types of articles. One common example is a box of adhesive bandages containing different types of bandages, wherein the wrappers of the bandages do not specify the type of bandage therein. A user not only must remove the bandage from the box, but typically must also hold the bandage up to the light to see through the wrapper to identify the bandage.

Such organizer systems and packagings have existed for many years without having presented a solution to the difficulties thereby presented in differentiating articles that are difficult to differentiate for the above-described reasons. Although it is recognized that boxes for food items may include menus identifying and differentiating the different types of food items contained therein, such menus have not been used for identifying and differentiating consumer items, such as bandages or first-aid supplies. More particularly, menus have not been used to identify and differentiate grouped articles, wherein the articles are not readily differentiable from one another. The present invention addresses the needs for identifying compartmentalized items and for differentiating among a plurality of groups of articles that are not otherwise readily differentiable from one another.

SUMMARY OF THE INVENTION

In accordance with the principles of the present invention, an organizer system is configured for organizing different articles that are not be readily distinguishable from one another so that the user can readily identify and select the desired article from the organizer system. In a preferred embodiment, the different articles are sorted by article type and each group of articles of the same type is stored in a separate compartment to separate the different types of articles from one another. The articles may be organized in an insert or tray that is removable from a shell portion of the container so the shell can be used for other purposes. Further in accordance with the principles of the present invention, a guide or chart or "menu" or other type of article identifying feature (hereinafter "menu" for the sake of convenience, without intent to limit) may be used to readily identify the articles contained in each of the various compartments.

In order to assure that the menu is readily accessible and facilitates selection of the desired article to the greatest extent and ease, the menu may be coupled to the container. In one embodiment, the menu may be provided in the lid of the container. More particularly, if desired, the menu may be formed separately from yet fixedly provided within the lid of the container.

In accordance with another aspect of the present invention, the organizer system may have a container with a hinged or flip-top lid that remains coupled with the holding portion of the container in which the articles are organized. The provision of a menu on the interior-facing surface of such lid is particularly helpful in assuring the menu is always readily accessible and arranged in close conjunction with the articles to be selected with the assistance of the menu.

In accordance with another aspect of the invention, the compartments may be formed by an insert separate from the container of the organizer system. The container may be formed from a sturdier material than that of the insert so that it lasts longer, whereas the material of the insert may be formed from a material that is less expensive yet easier to form into the desired compartments. As such, when the articles contained and/or stored in the organizer system of the present invention have all been used or removed, a new insert containing the same articles as before or different articles may be placed into the container. Alternatively, the container may be used for other purposes without the insert and compartments.

These and other features and advantages of the present invention will be readily apparent from the following detailed description of the invention, the scope of the invention being set out in the appended claims.

BRIEF DESCRIPTION OF THE DRAWINGS

The detailed description will be better understood in conjunction with the accompanying drawings, wherein like reference characters represent like elements, as follows.

DETAILED DESCRIPTION OF THE INVENTION

Figure 1:
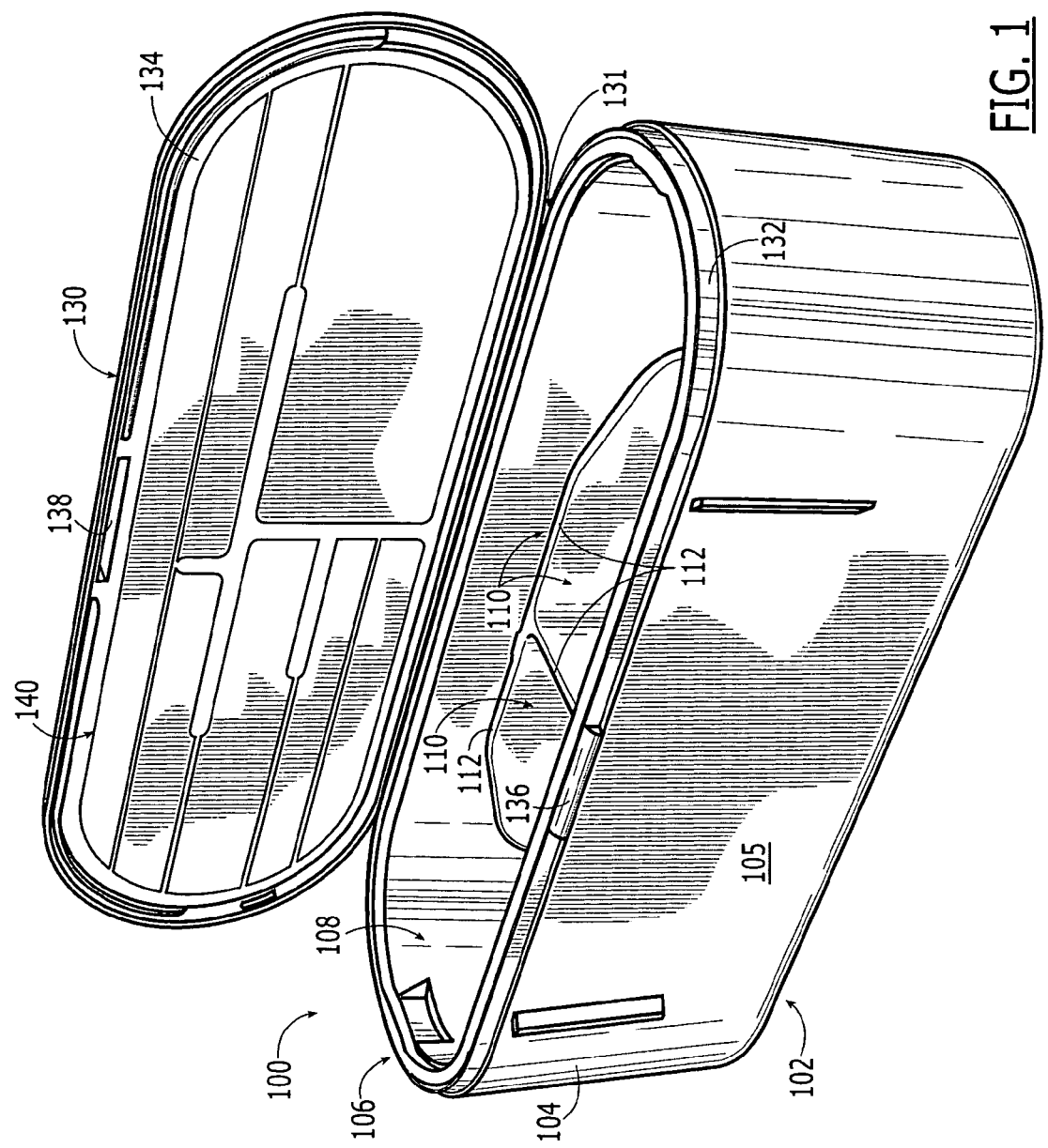
FIG. 1 is a perspective view of an organizer system formed in accordance with the principles of the present invention.

An exemplary organizer system 100 formed in accordance with the principles of the present invention is illustrated in FIG. 1. Organizer system 100 includes a container 102 having a base 104 configured for containing and/or storing articles therein, the articles being accessible via open end 106 of base 104. In accordance with the principles of the present invention, organizer system 100 is particularly designed to organize different articles to be contained and/or stored in base 104 so that a user may readily select the desired one of the various types of articles. In particular, it is preferable that organizer system 100 provide a manner of separating the articles by type for ready selection and removal from containment or storage within base 104. Accordingly, interior 108 of base 104 preferably is provided with two or more compartments 110, within each of which a different type of article or group of identical articles may be placed. Such compartments may be separated by dividing walls 112 or by any other element that serves to maintain different articles apart from one another. As will be described in further detail below, organizer system 100 may be formed specifically to contain and/or store articles in a manner that makes identification and differentiation of each article from the other difficult and inconvenient. Such intentional, typically undesirable, configuration may in fact be desirable for such reasons as space efficiency (resulting in cost savings in material as well) or for articles that are not readily distinguishable from one another anyway.

Figure 2:
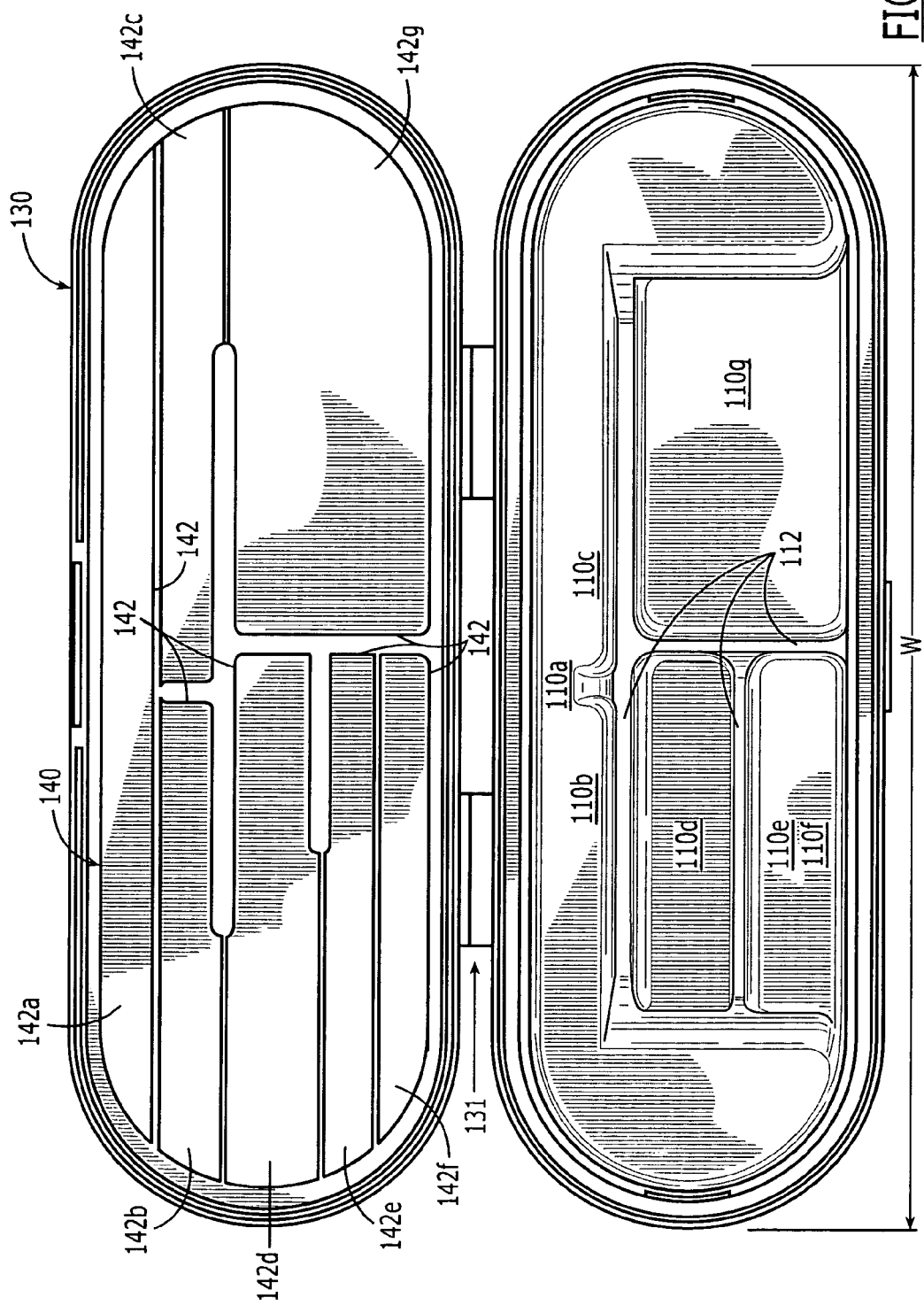
FIG. 2 is a top plan view of an organizer system as in FIG. 1 with the lid open and substantially horizontal.

As may be appreciated with reference to FIG. 2, compartments 110 may include a plurality of different compartments 110a, 110b, 110c, 110d, 110e, 110f, 110g (collectively, compartments "110") formed in various shapes and/or dimensions (either the same or different) and arranged with respect to one another in a preferably neat and organized manner. For instance, compartments 110 may be shaped and/or dimensioned to accommodate the particular shape and/or dimension of the given article to be contained therein. Thus, a compartment such as compartment 110a may be particularly convenient for an article that is longer than half the width W of base 104, as compartment 110a may extend the full width W of base 104. As may be further appreciated with reference to FIG. 2, and particularly with reference to exemplary compartments 110e and 110f, compartments formed in accordance with the principles of the present invention need not have dividing walls 112 therebetween. Moreover, the relative sizes and/or dimensions of compartments 110 may alternatively or additionally be selected based on the number of articles to be accommodated therein. For instance, compartment 110g of FIG. 2 may contain articles of essentially the same size as articles contained within any of compartments 110d, 110e, or 110f, but is larger than those compartments to contain more of the given article to be received therein than the number of articles to be received within any of compartments 110d, 110e, or 110f individually. It will be appreciated that the shapes, dimensions, sizes, and relative arrangement of compartments 110 with respect to one another is in no way limited by the illustrative arrangement in FIG. 2, such arrangement being merely one example of an arrangement of exemplary shaped and dimensioned and sized compartments 110.

Compartments 110 may be formed in any desired manner within base 104. For instance, compartment walls 112 may be formed integrally with base 104, such as by molding ribs or dividers into base 104 as a monolithic part of base 104. However, to enhance versatility of organizer system 100, compartments 110 may be formed as a separable, removable element insertable within a main "shell" portion of container 102. For instance, a separate wall structure may be insertable into and readily removable from base 104 to form compartments 110 as desired. A wall structure separate from base 104 may be in any desired form, such as a grid formed from paperboard or cardboard (such as used to separate breakable bottles from one another in a carton). Alternatively, exemplary insert 120 of FIGS. 3 and 4 may provide compartments 110 as separate parts selectively insertable into and removable from base 104. Insert 120 may be in the form of a shell in which walls 112 of compartments 110 are formed and which may be separable and removable from base. A separately formed shell 120 providing interchangeability of compartments 110 provides an added benefit of permitting ready refilling of base 104 with another newly filled insert 120, or a different insert (such as containing and/or storing different articles or having differently shaped compartments), and/or use of base 104 without any compartments therein (such as for purposes other than storing articles in separate compartments).

Additionally, if compartments 110 are formed separately from base 104 of container 102 (such as in the form of separable walls 112 or a separate insert 120), then the material of container 102 need not be the same as the material of walls 112 and/or compartments 110 and/or may be formed using a different manufacturing method. For instance, base 104 may be formed from a durable material (to permit extended use of container 102 even after all articles contained and/or stored therein have been removed and/or expended). Materials that may be used to form container 102 and base 104 include, without limitation, polypropylene and acrylonitrile butadiene styrene (ABS) resins, selection being determined on any of a variety of factors such as durability, rigidity, cost, etc. It will be appreciated that the present invention is not limited to a particular method for manufacturing container 102, and any desirable method (such as injection molding) may be used. Provision of compartments 110 via a separate insert 120 permits a less expensive material and/or method of manufacturing to be used for insert 120, which may be particularly desirable if insert 120 is to be replaced while container 102 is to be reused. For instance, in one embodiment, insert 120 may be formed of a high impact polystyrene (HIPS) that is thermoformed into the desired shape. Of course, other materials and other methods of manufacturing (such as injection molding) may be used instead without affecting the scope of the present invention.

Referring again to FIGS. 1-3, container 102 may be provided with a lid 130, if desired, such as to protect articles contained and/or stored within base 104, and/or to maintain the articles within container 102. Lid 130 preferably is configured to fit over and to close open end 106 of base 104.

Although lid 130 is shown to conform to the cross-sectional shape of base 104 (as may be appreciated particularly with reference to FIG. 2), such conforming shape is not necessary.

Figure 3:
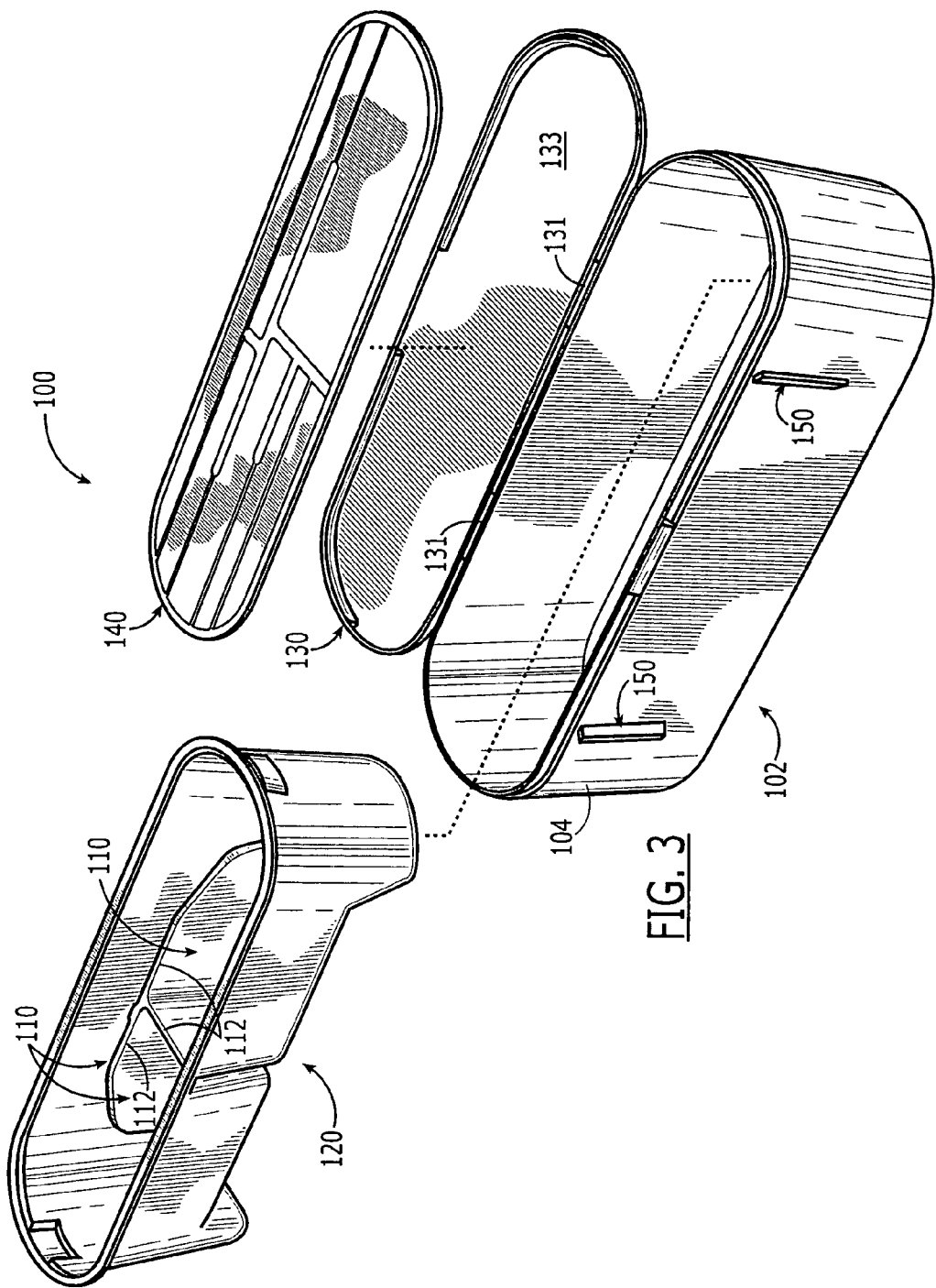
FIG. 3 is an exploded view of an embodiment of an organizer system formed in accordance with the principles of the present invention and in which compartments are formed by providing an insert element within a separately formed container shell, and a menu is formed separately from the container as well.
Figure 4:
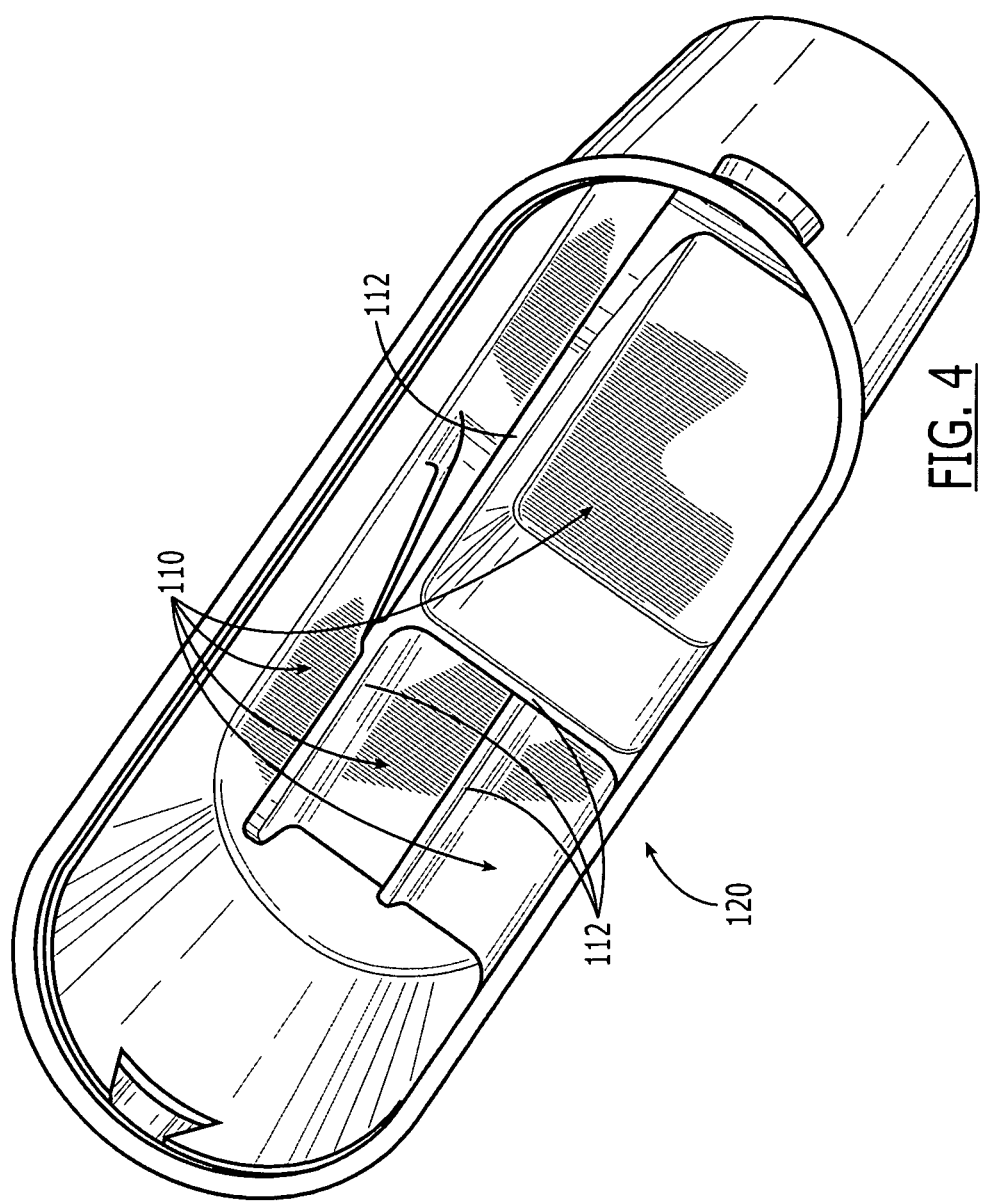
FIG. 4 is a top and side perspective view of an exemplary compartment insert showing the compartments formed therein.

Lid 130 may be fixedly coupled to base 104 of container 102 so that lid 130 remains with base 104 during the use and life of organizer system 100. For instance, the exemplary lid 130 of FIGS. 1-3 is hingedly coupled to base 104. In particular, a living hinge couples lid 130 and base 104 together (so that lid 130 and base 104 may be molded as a single piece). However, it will be appreciated that any other manner of coupling lid 130 and base 104 may be used. It will further be appreciated that even though exemplary lid 130 is illustrated as coupled to base 104 of container 102, lid 130 may be formed as a separate element that is completely removal from base 104 without any steps such as severing a connection therebetween.

If desired, lid 130 may be formed with alignment elements to assist in aligning and/or maintaining lid 130 over open end 106 of base 104. For instance, a raised surface or rib 132 may be provided on one of lid 130 and base 104 to fit into a recess 134 on the other of lid 130 and base 104. As may be appreciated, such rib and recess combination assures a particular alignment when used. Moreover, such rib and recess combination may impart a greater degree of friction between lid 130 and base 104, thereby maintaining lid 130 on base 104 in a closed configuration.

If articles are to be contained and/or stored within organizer system 100 in an airtight manner, a seal may be formed to interact with lid and main body of container. Such seal may be formed in any desired manner known in the art, the precise embodiment not affecting the scope of the present invention. The interaction of rib 132 with recess 134 described above may suffice, or addition of further sealing elements may be appropriate, as would be within the ken of one of ordinary skill in the art.

If desired, lid 130 may be formed with a closing mechanism that functions to maintain lid 130 in a closed position covering open end 106 of base 104 of container 102. For instance, a latch may be provided in any of a variety of manners known to those of ordinary skill in the art. In the exemplary embodiment of FIGS. 1-3, a detent 136 and mating recess 138 may be provided on lid 130 and base 104 to interact with each other as an internal hinge that maintains lid 130 closed over open end 106 of base 104. Although detent 136 may be provided on either one of lid 130 and base 104 and recess 138 may be provided on the other of lid 130 and base 104, if detent 136 is provided on base 104, and base 104 is formed of a relatively flexible material, then lid 130 may be opened by pressing on base wall 105 on which detent 136 is provided to release detent 136 from recess 138.

Figure 5:
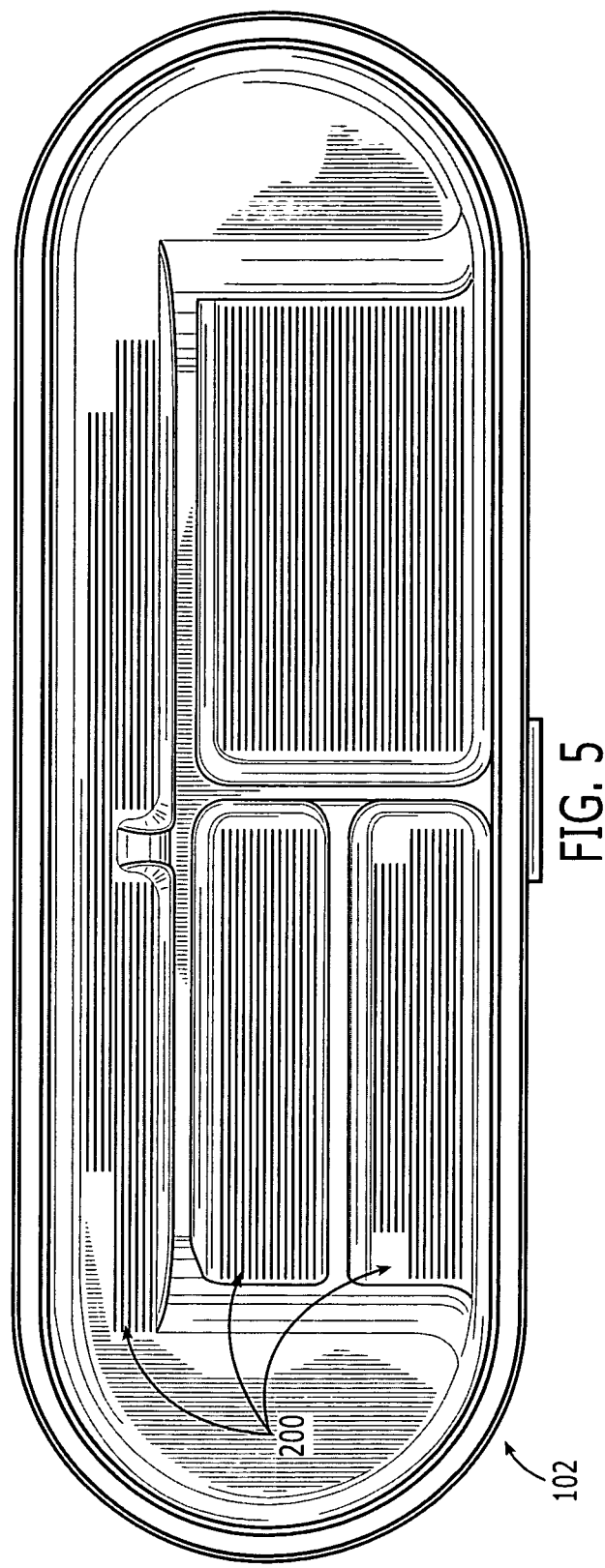
FIG. 5 is a top plan view of an alternate embodiment of an organizer system.

In accordance with the principles of the present invention, organizer system 100 is designed to address the unique disadvantages resulting from a plurality of different articles either being organized in a manner that interferes with ready differentiation of the articles, or being formed so that ready differentiation of the articles from one another is difficult, such as illustrated in the exemplary embodiment of FIG. 5. Specifically, articles 200 are arranged closely together in container 102 in a manner that does not permit ready identification of any individual article. The present invention intentionally disregards the disadvantages of such arrangement of articles 200 by providing a solution for readily identifying the articles despite such arrangement. In the exemplary embodiment of FIG. 14, organizer system 100 includes (1) a container 102 that preferably is particularly designed to contain and/or store different types of articles in a manner that does not permit ready identification of a particular desired article, and (2) a guide, such as menu 140, in conjunction with container 102 configured to assist a user in selecting a particular desired article from container 102. More particularly, although it is acknowledged that it is known to provide organizer systems for separating similar articles that are not identical to each other into compartments for each of the different types of articles, such separation still does not on its own assist the user in identifying the desired article. Moreover, the illustrated embodiment of the present invention is configured intentionally to organize articles in an efficient, space-saving manner that has the disadvantage of making identification of each article inconvenient and difficult. Because of such configuration, organizer system 100 of the present invention is particularly well-suited for storing a variety of articles that either do not have any identifying or differentiating indicia on them (such adhesive bandages, gauze pads, or sanitary napkins, which typically have wrappers that do not identify the type of adhesive bandage or sanitary napkin therein), or do not have a surface with identifying indicia exposed to the user while the article is stored within container 102 (such as pain relievers or other medications in bottles with caps or lids that look similar when viewed from above; or stationery goods such as labels; or tea bags stacked on their ends). The latter types of articles generally are stacked edgewise, or in a manner presenting a side smaller in dimension than the other sides of the article and thus not amenable to bearing identifying indicia. Such articles may be tightly packed and must be individually drawn out of interior 106 of base 104 to be identified. The present invention is particularly designed for storing such articles and for providing a menu 140 that heretofore has not been provided in conjunction with such articles stored in such manner. Menu 140 facilitates ready selection of a desired one of a plurality of different types of articles without the need to remove and/or to examine the article.

Given the nature of the articles for which organizer system 100 is particularly suited, no pictures are necessary on the menu since a picture likely will not provide useful information in any event. However, if desired, menu 140 may be configured to have regions corresponding (such as in shape and/or relative position) to compartments 110, thus potentially further facilitating use of menu 140 in identifying a desired article.

It is helpful to maintain such an uncommon menu (in that no pictures of the articles identified by the menu is provided) in a particular orientation to facilitate matching of items on the menu with articles within container 102, and particularly within the individual compartments 110 therein. To further facilitate use, menu 140 may be coupled to organizer system 100. In the embodiment illustrated in FIGS. 1 and 2, menu 140 may be coupled to container 102 to remain therewith in a particular orientation. Such positioning is in contrast with menus, such as used in boxes of chocolate, that are separate inserts provided within the box. Coupling of menu 140 with container 102 may be achieved in any of a desired number of manners, such as via lid 130 (lid 130 in turn being coupled to base 104 of container 102 either fixedly or removably), or by being fixed directly to base 104 (such as by being adhered to wall 105 of base 104, such as if a lid is not provided). As such, menu 140 is always readily available for reference purposes.

As a further feature of coupling menu 140 to container 102 via a fixedly coupled lid 130, lid 130 may be provided in a manner that permits lid 130 to maintain itself in an open position. The manner of coupling lid 130 to base 104 may achieve such function in a variety of manners. For instance, a hinge that can maintain lid 130 in a fixed open position may be used. If a living hinge is used, such as living hinge 131 of FIGS. 1-3, then the material thereof may be selected to permit selective positioning and maintenance of the selected positioning (such as by virtue of a degree of memory in the material). One such material that permits repositioning of a living hinge is polypropylene, although other materials may be used in the present invention instead. Accordingly, lid 130 remains open on its own without the necessity of the user actively holding lid 130 open. A user thus may readily peruse menu 130 and select an article without worrying if lid 130 will close on its own.

It will be appreciated that menu 140 may be formed in any desired manner with respect to container 102. In the illustrated embodiment of FIG. 3, menu 140 is formed as a separate element that may then be secured to the interior surface 133 of lid 130. An economical and efficient manner of forming a menu as an element separate from container 102 is by printing the graphics of menu 130 on paperboard (or another suitable material) and coupling menu 130 to interior surface 133 of lid 130. Coupling may be achieved in any desired manner, such as by permanent adhesive, releasable adhesive, tape, etc. If replacement of insert 120 of the embodiment of FIG. 3 is desirable, then releasable adhesive gives the added benefit of ready removal and replacement of menu 140 with another menu that corresponds to the replacement insert and the articles contained therein. Other manners of forming menu 140 are well within the scope of the present invention. For instance, the menu may be embossed, printed, and/or molded (using any know manner of embossing, imprinting, or molding) within interior surface 133 of lid 130, thus forming an integral part of lid 130.

If a lid is not necessary for container 102, it will be appreciated that the menu may be provided on a wall of container 102 so that the menu is readily available for reference purposes to assist a user in selecting a desired article from within base 104. For instance, a menu may be provided on wall 105 of base 104 arranged to facilitate use of the menu in identifying a desired article within base 104.

In accordance with another aspect of the present invention, container 102 may be coupled to another container such as by means of coupling elements 150 as illustrated in the exemplary embodiment of FIG. 3. Coupling elements 150 may be formed in any desired manner to provide selective coupling and decoupling of containers together and apart from each other. The exemplary illustrated coupling elements 150 are formed by providing angularly outwardly extending wings on one side of the container (as illustrated in FIG. 3) and angularly inwardly extending wings on the other side. The angularly outwardly extending wings of one container interengage with the angularly inwardly extending wings of another container by moving the containers with respect to each other in a vertical direction. If desired, a stop wall may be provided so that once two containers are coupled together, the stop wall prevents the containers from sliding apart from each other.

While the foregoing description and drawings represent exemplary embodiments of the present invention, it will be understood that various additions, modifications and substitutions may be made therein without departing from the spirit and scope of the present invention. In particular, it will be clear to those skilled in the art that the present invention may be embodied in other specific forms, structures, arrangements, proportions, and with other elements, materials, and components, without departing from the spirit or essential characteristics thereof. For instance, the shape and dimensions of the exemplary container shown in the FIGURES are illustrative only. Moreover, various modifications to the lid, such as manners of coupling the lid to the main body of the container, or the manner of maintaining the lid in the closed position, are within the scope of the present invention. It will be appreciated that the shape and dimensions of any of the elements of the present invention may be modified in any desired manner, such as to accommodate differently sized or shaped articles. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. For example, elements shown as integrally formed may be constructed of multiple parts or elements shown as multiple parts may be integrally formed, the operation of elements may be reversed or otherwise varied, the size or dimensions of the elements may be varied. The presently disclosed embodiments are therefore to be considered in all respects as illustrative and not restrictive, the scope of the invention being indicated by the appended claims, and not limited to the foregoing description.

What is claimed is:

1. An organizer system for individually wrapped adhesive bandages, said organizer system comprising:
    a container having a container base with a plurality of compartments therein;
    a plurality of individually wrapped first adhesive bandages stacked and tightly packed edgewise in a first of said plurality of compartments within said container base;
    a plurality of individually wrapped second adhesive bandages different from said first adhesive bandages and stacked and tightly packed edgewise in a second of said plurality of compartments within said container base; and
    a menu identifying and distinguishing the wrapped first and second adhesive bandage in accordance with the compartment in which said respective individually wrapped adhesive bandages are stacked and tightly packed edgewise, said menu comprising the sole means of differentiating the individually wrapped first adhesive bandages from said individually wrapped second adhesive bandages without removing an individual individually wrapped adhesive bandage from its compartment to examine said adhesive bandages;
    wherein:
    said plurality of individually wrapped first adhesive bandages are wrapped in first wrappers without bandage-identifying indicia thereon;
    said plurality of individually wrapped second adhesive bandages are wrapped in second wrappers without bandage-identifying indicia thereon;
    said plurality of individually wrapped first adhesive bandages are not readily distinguishable from said individually wrapped second adhesive bandages upon examination of said first and second wrappers; and
    said plurality of individually wrapped first adhesive bandages are not readily distinguishable from said individually wrapped second adhesive bandages as stacked and tightly packed edgewise in said organizer system despite being contained in separate compartments and being different adhesive bandages.

2. An organizer system as in claim 1, wherein said individually wrapped adhesive bandages are positioned with only an unmarked surface visible when said individually wrapped adhesive bandages are arranged within said compartments.

3. An organizer system as in claim 1, wherein said individually wrapped adhesive bandages are packaged in a wrapper without identifying indicia.

4. An organizer system as in claim 1, wherein:
said container base has an open end through which said individually wrapped adhesive bandages are accessible; and
said organizer system further comprises a lid configured to close said container base open end.

5. An organizer system as in claim 4, wherein:
said lid is coupled to said container base; and
said menu is provided on said lid.

6. An organizer system as in claim 5, wherein:
said lid has an interior surface facing said compartments when said lid closes said open end of said container base; and
said menu is provided on said interior surface of said lid.

7. An organizer system as in claim 6, wherein said menu is provided on said interior surface of said lid as a separate element.

8. An organizer system as in claim 6, wherein said menu is provided directly on said interior surface of said lid by embossing, imprinting, or molding.

9. An organizer system as in claim 1, wherein said compartments are formed separately from said container base.

10. An organizer system as in claim 9, wherein said compartments are formed in an insert selectively insertable into and removable from said container base.

11. An organizer system as in claim 1, wherein: each compartment contains a different individually wrapped article; and said menu identifies the individually wrapped article contained in each compartment.

12. An organizer system as in claim 11, wherein said menu has regions corresponding to said compartments and identifies on each region the article contained in the corresponding compartment.

13. An organizer system as in claim 1, wherein:
said menu has a plurality of shaped regions corresponding at least to each of said first and second shaped compartments;
a shaped region of said menu corresponding to said first of said plurality of compartments bears indicia identifying the first adhesive bandages contained in said first of said plurality of compartments; and
a shaped region of said menu corresponding to said second of said plurality of compartments bears indicia identifying the second adhesive bandage contained in said second of said plurality of compartments.

14. An organizer system as in claim 5, wherein said lid is hingedly coupled to said container base.

* * * * *